United States Patent
Street

Patent Number: 6,154,315
Date of Patent: *Nov. 28, 2000

[54] APPARATUS AND METHOD FOR STEREOSCOPIC ENDOSCOPY

[76] Inventor: Graham S. B. Street, Impstone House, Pamber Road, Silchester, Reading, Berkshire, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/165,311

[22] Filed: Oct. 2, 1998

Related U.S. Application Data

[63] Continuation of application No. PCT/GB97/00915, Apr. 2, 1997.

[30] Foreign Application Priority Data

Apr. 3, 1996 [GB] United Kingdom .................... 9607089
Jul. 22, 1996 [GB] United Kingdom .................... 9615338

[51] Int. Cl.[7] ............................ G02B 27/26; G02B 27/22; A61B 1/04; H04N 13/00
[52] U.S. Cl. .......................... 359/465; 359/469; 600/111; 348/45
[58] Field of Search ....................................... 359/469, 465, 359/376, 377, 378; 600/111; 348/45

[56] References Cited

U.S. PATENT DOCUMENTS

| | | | |
|---|---|---|---|
| 5,222,477 | 6/1993 | Lia ............................................... | 128/6 |
| 5,610,765 | 3/1997 | Colucci .................................... | 359/497 |
| 5,617,387 | 4/1997 | Morita et al. ............................ | 359/495 |
| 5,649,897 | 7/1997 | Nakamura et al. ...................... | 600/111 |
| 5,715,029 | 2/1998 | Fergason ................................. | 359/495 |

FOREIGN PATENT DOCUMENTS

| | | |
|---|---|---|
| 0577268A1 | 1/1994 | European Pat. Off. . |
| 0582148A1 | 2/1994 | United Kingdom . |

*Primary Examiner*—Cassandra Spyrou
*Assistant Examiner*—Jennifer Winstedt

[57] ABSTRACT

Apparatus and method for providing stereo-image pairs, typically for use in endoscopy. A birefringent optical component creates two virtual pupils to provide spaced view points of an object field through a single real pupil, the light from each of the two view points having a respectively different polarization. The birefringent component may be in the form of a calcite slab or comprise liquid crystal material. By suitable orientation of two such components with respect to each other, the path lengths for the two polarizations of light may be made equivalent and rotation of the planes of polarization of this light through 90 degrees by means disposed between the birefringent components can improve the performance of the system. The rotation device may comprise a half-wave plate or a layer of liquid crystal material. By tilting the slab of calcite, the observer may be provided with a change in view point and, thereby, some motion parallax. In one embodiment of the invention, a polarizing beam splitter directs light corresponding to each of the two view points to respectively different CCD's, following its passage through the single pupil.

15 Claims, 3 Drawing Sheets

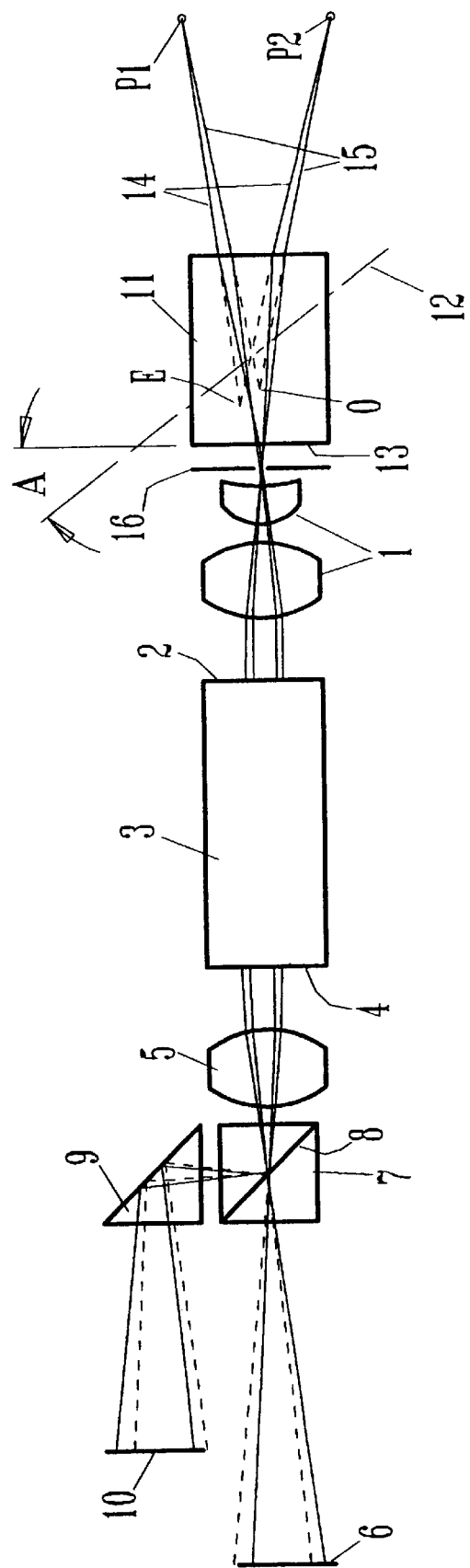
Fig. - 1 -

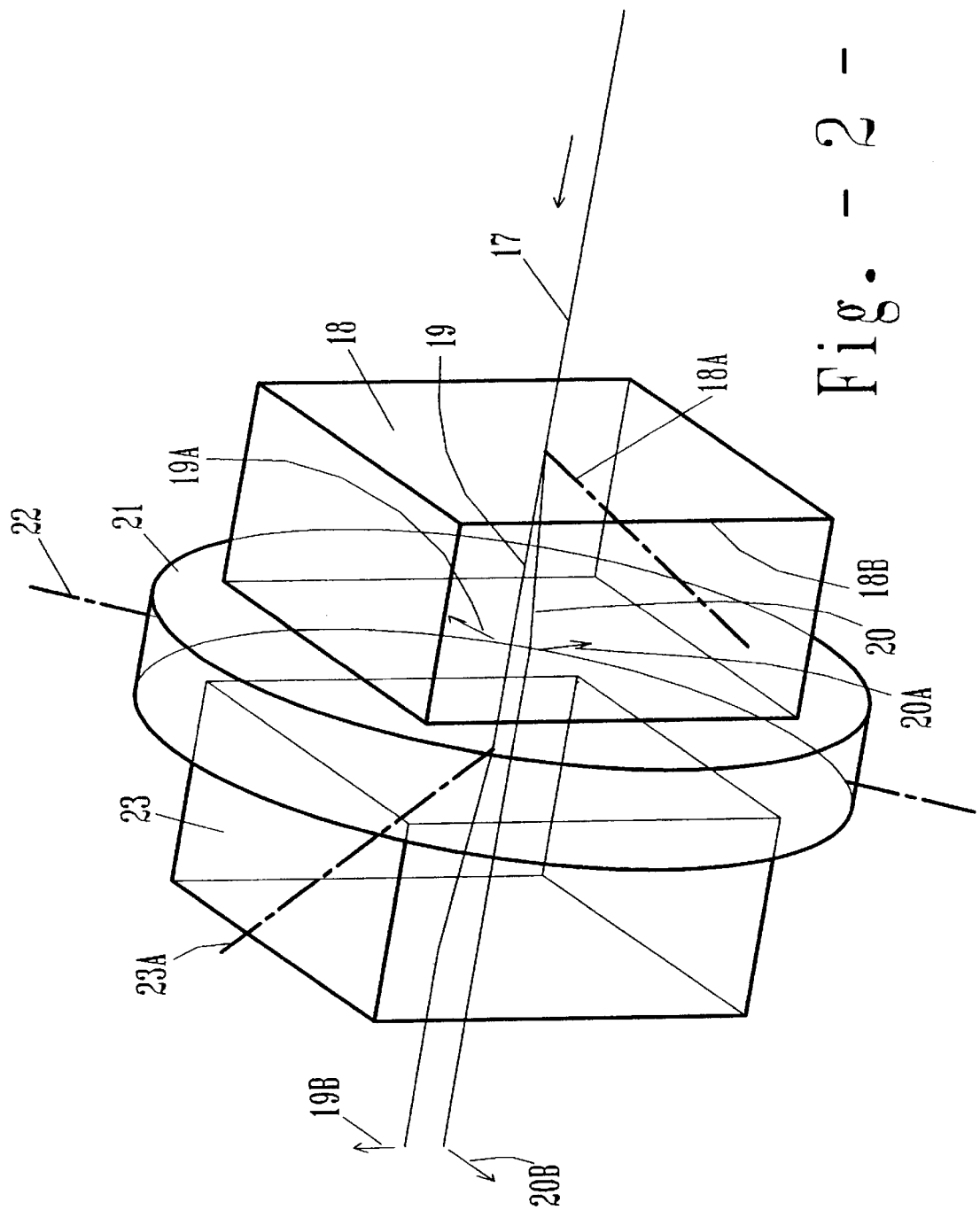

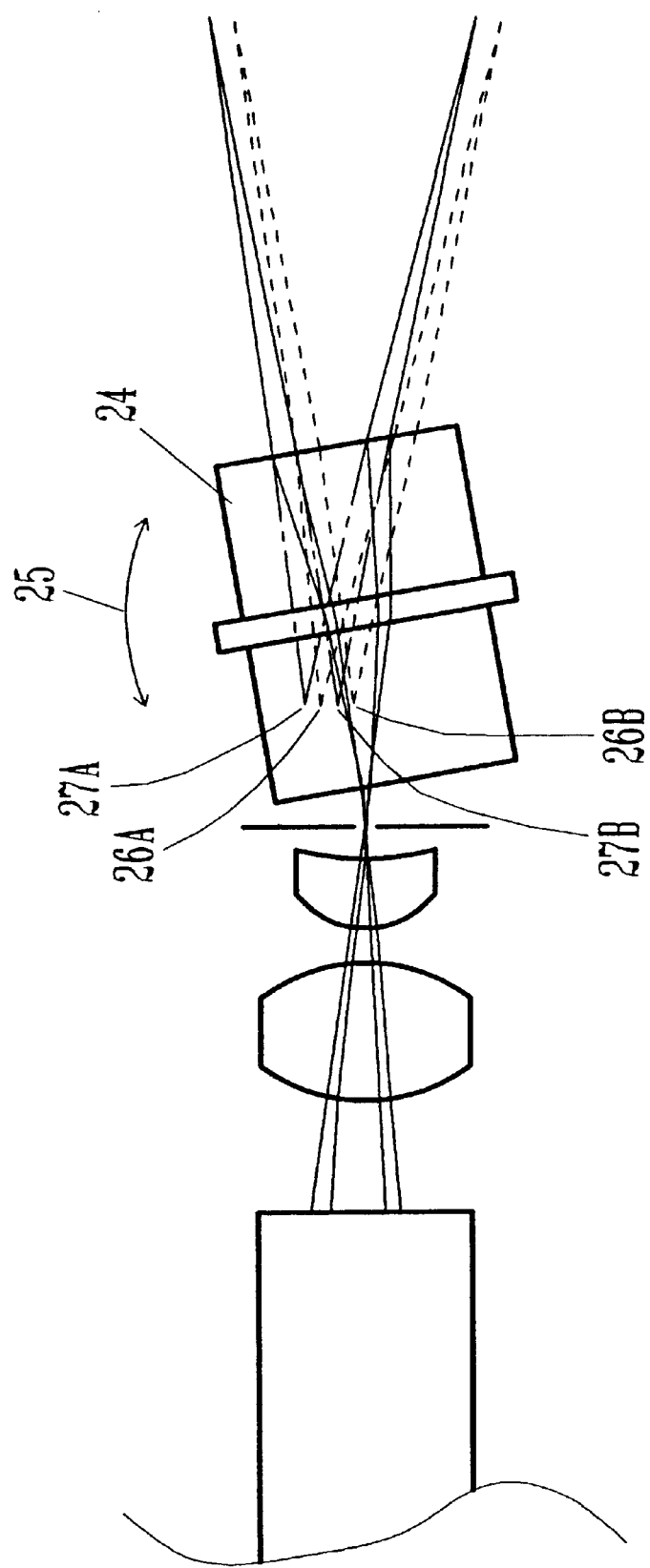
Fig. - 3 -

APPARATUS AND METHOD FOR STEREOSCOPIC ENDOSCOPY

This application is a Continuation of PCT application No. PCT/GB97/00915 filed on Apr. 2, 1997, which designated the United States and on which priority is claimed under 35 U.S.C. § 120, the entire contents of which are hereby incorporated by reference.

This invention relates to the field of stereoscopic imaging and in particular to the provision of a stereoscopic image from an endoscope or similar optical relay system.

BACKGROUND

Both in the medical field and in certain industrial applications it is desirable to relay an image through a tube of substantial length, such as an endoscope. This is used to inspect and manipulate items of interest in locations which are not easily accessible by other means. In the medical field, the opportunity to reduce patient trauma and after care, by employing so-called Minimally Invasive techniques, is of major interest. One of the more important aids to manipulation, when doing so normally, is binocular vision. Each eye sees a slightly different perspective of the subject, which allows the precise determination of distance and depth.

An endoscope typically comprises a series of imaging and relay lenses, which transfer an image, usually wide angle, from the distal end of the instrument to the eye piece at the other end. Here, there is a pupil. What is meant by pupil is an effective aperture which may be a relayed image of a physical stop at any position in the optical system. Conveniently, the user may place his eye at a pupil of the system to observe the image. Often the eye's function is assumed by a small video camera suitably coupled to the optical system of the endoscope. The simplest way, conceptually, to provide two different perspective views of a subject trough an endoscope, is to duplicate the optical relay system, with both systems running side by side down the instrument. This approach is often adopted, but requires careful alignment of one system's optical axis to that of the other, in order to provide the correct correspondence between different points in each image. A second approach, which is also well known, is to subdivide the pupil of the system, either sequentially using one camera or by sending the two slightly different images, formed from light from the different portions of the pupil, to respectively different cameras, simultaneously.

In EP-A-0 577 268 (Dumbreck) an example of such apparatus is provided in which the exit pupil of a monocular viewing device such as an endoscope is divided into two halves and the light from each half is used to form an image seen from a slightly different view point to that provided by the other. As an aid to separating the light from the different halves of the pupil, the use of a two-part polarising plate is described in which, for example, one direction of polarisation is imparted to the light from the left half of the pupil, and an orthogonal direction is imparted to the light passing through the right half. A polarisation selective beam splitter, such as a Nicol prism, may then be used to separate these polarised components to form separate images for viewing by left and right eyes respectively.

The disadvantage of such an approach is that, whereas the majority of alignment problems are avoided, the stereopsis (difference in perspective) achieved is limited to that occurring within the dimensions of the pupil. This can have a diameter as small as 0.3 mm or less at the distal end, where the subject will typically be at a range of distances of up to 60 mm or more. The effective separation of the two halves of the pupil is of the order of 0.15 mm in the above example. For the normal level of stereopsis at 15 mm, a separation of at least 0.5 mm is desirable. The above identified prior art does not reveal how to increase the separation of the two view points beyond that which can be achieved within the overall dimensions of system's pupil. Additionally, where polarisation is used to aid in the separation of light rays corresponding to the different view points, the useful light for the formation of the image corresponding to each eye will in practice be reduced by more than a factor of two.

In Patent Application GB 9607089.1 (Street), an embodiment of endoscopic apparatus is disclosed which, for stereoscopic use, may conveniently include the use of a birefringent component for the provision of two points of view. This description develops the invention further and overcomes some of the attendant difficulties associated with its practical implementation. Unlike the limitations imposed by the apparatus of EP-A-0 577 268, a view point separation greater than the dimension of a single pupil may be achieved and light from the whole of this pupil can contribute to each of the images viewed.

SUMMARY OF THE INVENTION

It is an object of the invention to provide a degree of stereopsis through a small entrance pupil which would not be achievable using pupil segmentation techniques alone.

It is a further object of the invention, in certain embodiments, to provide an endoscope which provides a measure of motion parallax when suitably coupled to movement of the observer. Motion parallax is experienced when moving the observer's viewpoint during observation, thus causing objects at different distances to move relative to each other within the retinal image.

STATEMENTS OF INVENTION

Thus according to the present invention there is provided apparatus for stereoscopic imaging comprising a system for forming and relaying an image of an object field and means having a single pupil through which said object field is viewed characterised in that displacement means is provided between said single pupil and said object field, said displacement means being effective to create a first virtual pupil providing a first view point of said object field and a second virtual pupil spaced from said first virtual pupil providing a second view point of said object field spaced from said first view point; said first virtual pupil being a virtual image of said single pupil for light polarised in a first direction and said second virtual pupil being a virtual image of said single pupil for light polarised in a second direction distinct from said first direction, so that substantially every point of said single pupil is provided with light corresponding to both of said view points.

Preferably the displacement means comprises birefringent material.

Advantageously the birefringent material is in the form of a slab.

In certain embodiments the birefringent material is calcite. In some embodiments the birefringent material comprises a liquid crystal.

The displacement means may comprise a composite of at least two birefringent components so orientated as to ensure that the path lengths through the composite for the two polarisations of light are the same.

Advantageously the composite includes means for rotating the planes of polarisation of the light through 90 degrees disposed between two of the birefringent components.

In some embodiments the rotation means comprises a half-wave plate. Alternatively, the rotation means comprises liquid crystal material.

According to a further aspect of the invention the displacement means is changeable to provide motion parallax. The change may be effected by tilting the slab of birefringent material.

According to another aspect of the invention the light corresponding to each of the two view points is directed into respectively different optical paths by a polarisation selective component following passage through the single pupil. Advantageously the polarisation selective component is a polarising beam splitter.

DESCRIPTION OF PREFERRED EMBODIMENTS

The invention will now be described with reference to FIGS. 1 to 3 in which:

FIG. 1 shows diagrammatically an endoscope constructed in accordance with the invention.

FIG. 2 is a birefringent element used in a preferred embodiment of the invention.

FIG. 3 illustrates how motion parallax is provided in accordance with the invention.

An endoscope constructed in accordance with the invention is illustrated in FIG. 1. Points P1 and P2 in an object field are imaged by an objective lens assembly 1 to the first image plane 2 of a relay system 3. For convenience this relay system is shown as a short assembly, whereas in reality it would be quite long. This is assumed to reproduce the image formed at plane 2 at an exit plane 4. A lens 5 produces an image of the object field on a CCD array 6, through a polarising beam splitter 7. Light with its polarisation direction in the plane of the diagram is transmitted by splitter 7. Light with its polarisation direction orthogonal to the diagram is reflected from the internal face 8 of splitter 7. This light forms, via a reflecting prism 9, another image of the object field on a second CCD array 10. If it were not for the properties of a special component positioned in the optical path intermediate the object field and objective assembly 1, these two images would be the same. A birefringent slab of calcite 11, with its optic axis 12 tilted out of the transmitting face 13 of slab 11 by an angle A of approximately 38°, causes light from points P1 and P2 to travel via two distinct optical paths 14 and 15 before reaching the pupil of the optical system at plane 16. One set of paths 15 comprise ordinary rays of light which pass through slab 11 in a conventional manner according to Snell's laws of refraction and are polarised in a direction orthogonal to the diagram. The second set of paths 14 are subject to an elliptical indicatrix of refraction due to the birefringence of the calcite and comprise light rays polarised in the plane of the diagram. The difference between the refractive index along optic axis 12 and that at right angles to it causes these so-called Extraordinary rays to be deflected upon entering slab 11 by about 6° towards axis 12 in addition to any deflection expected from Snell's laws. When exiting slab 11, the Extraordinary rays loose this additional deflection and become parallel to their Ordinary counterparts. Consequently a lateral displacement has occurred which, when viewed from the object field, is equivalent to the endoscope presenting two pupils displaced from one another by a distance which depends on the birefringence of slab 11 and its thickness. In FIG. 1 the centres of these two virtual pupils are denoted as O and E respectively. It will be apparent that the effective point of view seen through the endoscope is different for the Extraordinary rays 14 to that provided by the Ordinary rays 15. The perspective separation achieved is 0.105 mm for each mm of thickness of slab 11 and accordingly a 5 mm thickness is found to provide a 0.525 mm shift between the two effective pupil positions. This is more than adequate for the generation of a pair of stereo images of subject matter at working distances of 5 to 20 mm from the endoscope. Pupil size is typically about 0.2 mm for a small endoscope and this does not provide scope for more than 0.1 mm of perspective separation. The stereo image pair is provided by the two CCD's 6 and 10, each receiving rays having a plane of polarisation orthogonal to those received by the other, this being effected by the polarising beam splitter 7. The birefringence of the calcite slab 11 of FIG. 1 has a second consequence. The equivalent thickness in air of slab 11 is different for the Extraordinary rays and the Ordinary rays. When the distance of the subject matter is much greater than the slab's thickness, or, more specifically, when light from object points is collimated on passing through the material, either by these points being distant or collimated by an intermediate lens (which can only be true for one distance), this has little significance. However, for near field objects at a variety of distances which is the very nature of the endoscopic application, this consequence has a draw back. There will be different scale changes for equivalent points in the two observed images. One of these images is intended for the observer's left eye, whereas the other is for the right eye. There should only be lateral disparity and no vertical disparity, the inevitable consequence at the top and bottom of the image if two images are not the same size. Whilst this can be corrected for one distance, the simple arrangement of FIG. 1 does not achieve this for arbitrary distance. This problem can be overcome by splitting the calcite into two slabs, and rotating one with respect to the other. If this rotation is 90°, the Extraordinary ray in the first becomes the Ordinary ray in the second and all rays experience the same equivalent thickness in air. The total displacement however is reduced to the vector sum of two displacements orthogonal to each other, each of half the original magnitude. The resultant effect is $\sqrt{(½)}$ of its original value.

The alternative embodiment of FIG. 2 avoids this reduced effect. The sub-assembly is oriented for the sake of clarity to split the light which passes through it in a vertical plane. In practice, it would be used horizontally to provide two horizontally spaced points of view. Ray 17 from the object field enters calcite slab 18 which has its optic axis 18A turned through 38° in a clockwise direction with respect to the vertical edge 18B. Two rays result. The first is the ordinary ray 19 which, for the normal incidence case continues in the same direction. Its plane of polarisation is horizontal as indicated by arrow 19A. The extraordinary ray 20 is bent downwards and is vertically polarised as indicated by arrow 20A. Both rays enter a half wave plate 21 with its principle axis 22 at 45° to the horizontal and vertical. As a result, the direction of polarisation for both rays is turned by 90° and on entering the second calcite slab 23, which has its optic axis 23A in a vertical plane containing the optic axis 18A of slab 18, what was the extraordinary ray 20 becomes the ordinary ray for slab 23. Likewise ray 19 becomes the extraordinary ray for the second calcite slab. Its optic axis 23A is tilted in the opposite direction from the vertical to that of slab 18 and, as a result, the two rays are separated further, whilst the optical path length for both is the same through the composite assembly. The polarisation directions of the rays exiting the optical assembly are orthogonal to those on entry, as indicated by arrows 19B and 20B. An alternative to the use of the half wave plate 21 is to use a twisted liquid crystal to turn the plane of polarisation of the light through 90°.

FIG. 3 shows how an optically thick component such as the sub-assembly of FIG. 2 can be incorporated in an endoscope to provide, in addition to two view points, a change in these view points, without moving the whole instrument. Sub-assembly 24 constructed in accordance with the principles of FIG. 2, may be tilted as indicated by arrows 25. This has the effect of moving the original positions 26A and 26B of the two virtual pupil positions to positions 27A and 27B, thus providing two new view points of the object field. Such tilting of assembly 24 can be driven by changes in the viewer's co-ordinates, which are conveniently provided by a head or eye tracking system.

Whilst components comprised of naturally occurring calcite are employed in the illustrated embodiments of this invention and the birefringence of this material produces the necessary separation between two points of view of an object field, liquid crystal materials are known to exhibit high levels of birefringence, when their molecules are suitably aligned. Suitable arrangements of optical structures incorporating such materials can be used to provide separation between orthogonally polarised image components in accordance with this invention.

What is claimed is:

1. Apparatus for stereoscopic imaging comprising a system for forming and relaying an image of an object field and means having a single pupil through which said object field is viewed characterised in that displacement means is provided between said single pupil and said object field, said displacement means being effective to create a first virtual pupil providing a first view point of said object field and a second virtual pupil spaced from said first virtual pupil providing a second view point of said object field spaced from said first view point; said first virtual pupil being a virtual image of said single pupil for light polarised in a first direction and said second virtual pupil being a virtual image of said single pupil for light polarised in a second direction distinct from said first direction, so that substantially every point of said single pupil is provided with light corresponding to both of said view points.

2. Apparatus as claimed in claim 1 wherein the displacement means comprises birefringent material.

3. Apparatus as claimed in claim 2 in which the birefringent material is in the form of a slab.

4. Apparatus as claimed in claim 3 wherein the birefringent material is calcite.

5. The apparatus of claim 3 in which the displacement means is changeable to provide motion parallax and the change is effected by tilting the slab.

6. Apparatus as claimed in claim 2 wherein the displacement means comprises a composite of at least two birefringent components so orientated as to ensure that the path lengths through the composite for the two polarisations of light are the same.

7. Apparatus as claimed in claim 6 in which the composite includes means for rotating the planes of polarisation of the light through 90 degrees disposed between two of the birefringent components.

8. Apparatus as claimed in claim 7 in which the rotation means comprises a half-wave plate.

9. Apparatus as claimed in claim 7 in which the rotation means comprises liquid crystal material.

10. Apparatus as claimed in claim 2 in which the birefringent material comprises liquid crystal material.

11. Apparatus as claimed in claim 2 in which the displacement means is changeable to provide motion parallax.

12. Apparatus as claimed in claim 1 in which light corresponding to each of the two view points is directed into respectively different optical paths by a polarisation selective component following passage through the single pupil.

13. Apparatus as claimed in claim 12 in which the polarisation selective component is a polarising beam splitter.

14. A method for viewing a stereoscopic image comprising forming and relaying an image of an object field through a single pupil characterised by providing displacement means intermediate said single pupil and said object field; creating a first virtual pupil and thereby providing a first view point of said object field and a second virtual pupil spaced from said first virtual pupil thereby providing a second view point of said object field spaced from said first view point; and providing substantially the whole of said single pupil with light polarised differently for each of said view points.

15. The method of claim 14 which includes providing a slab of transparent material within the displacement means; tilting said slab in accordance with the motion of an observer, thereby providing motion of a virtual image of said pupil, having a respective view point of said object field; and providing motion parallax, within the relayed image thereof.

* * * * *